(12) United States Patent
Tsukamoto et al.

(10) Patent No.: US 9,020,098 B2
(45) Date of Patent: Apr. 28, 2015

(54) RADIATION IMAGING APPARATUS

(71) Applicant: Canon Kabushiki Kaisha, Tokyo (JP)

(72) Inventors: Takeo Tsukamoto, Kawasaki (JP); Ichiro Nomura, Atsugi (JP); Mitsuaki Amemiya, Saitama (JP); Akira Miyake, Nasukarasuyama (JP); Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 141 days.

(21) Appl. No.: 13/791,070

(22) Filed: Mar. 8, 2013

(65) Prior Publication Data
US 2013/0243156 A1   Sep. 19, 2013

(30) Foreign Application Priority Data

Mar. 13, 2012 (JP) ................... 2012-055717

(51) Int. Cl.
- *G01N 23/20* (2006.01)
- *G21K 1/00* (2006.01)
- *G01N 23/04* (2006.01)
- *G21K 1/06* (2006.01)

(52) U.S. Cl.
CPC ........ *G21K 1/00* (2013.01); *G01N 23/04* (2013.01); *G21K 1/06* (2013.01); *G21K 2201/064* (2013.01)

(58) Field of Classification Search
USPC ................................. 378/84–85, 70
See application file for complete search history.

(56) References Cited

U.S. PATENT DOCUMENTS

| | | | |
|---|---|---|---|
| 5,570,408 A | 10/1996 | Gibson | 378/145 |
| 7,050,537 B2 | 5/2006 | Tsujii | |
| 7,104,686 B2 | 9/2006 | Watanabe et al. | |
| 7,315,606 B2 | 1/2008 | Tsujii | |
| 7,386,157 B2 | 6/2008 | Tago et al. | |
| 7,564,998 B2 | 7/2009 | Tsujii | |
| 7,742,566 B2 | 6/2010 | Hopkins et al. | 378/84 |
| 7,873,146 B2 | 1/2011 | Okunuki et al. | |
| 7,945,015 B2 | 5/2011 | Tsujii et al. | |
| 7,970,100 B2 | 6/2011 | Tsujii et al. | |
| 7,991,120 B2 | 8/2011 | Okunuki et al. | |
| 8,472,585 B2 | 6/2013 | Ogura et al. | |
| 2011/0058727 A1 | 3/2011 | Tsujii | |
| 2011/0216884 A1 | 9/2011 | Tsujii et al. | |
| 2012/0051499 A1* | 3/2012 | Lee et al. | 378/16 |
| 2012/0121069 A1 | 5/2012 | Aoki et al. | |

(Continued)

FOREIGN PATENT DOCUMENTS

| | | |
|---|---|---|
| JP | H10-508947 | 9/1998 |
| JP | 2004-89445 | 3/2004 |

*Primary Examiner* — Hoon Song
(74) *Attorney, Agent, or Firm* — Fitzpatrick, Cella, Harper & Scinto

(57) ABSTRACT

A radiation imaging apparatus according to the present invention includes a radiation source, a reflective structure where at least three reflective substrates are arranged with an interval and radiations being incident into a plurality of passages whose both sides are put between the reflective substrate are reflected and parallelized by the reflective substrate at both sides of the passage to be emitted from the passage, a radiation detector, and an image construction unit that constructs an image of an object based on an intensity of the radiation which is emitted from each of the passages, transmits the object and is detected by the radiation detector. When one edge of the reflective structure is an inlet of the radiation and the other edge is an outlet of the radiation, a pitch of the reflective substrates at the outlet is larger than a pitch at the inlet.

8 Claims, 8 Drawing Sheets

(56) References Cited

U.S. PATENT DOCUMENTS

| | | |
|---|---|---|
| 2012/0307974 A1 | 12/2012 | Yamazaki et al. |
| 2012/0318990 A1 | 12/2012 | Tsujii et al. |
| 2013/0003927 A1 | 1/2013 | Tsujii |
| 2013/0028499 A1 | 1/2013 | Tsujii et al. |
| 2013/0163719 A1 | 6/2013 | Tsujii |
| 2013/0197342 A1 | 8/2013 | Tsujii |

* cited by examiner

RADIATION IMAGING APPARATUS

BACKGROUND OF THE INVENTION

1. Field of the Invention

The present invention relates to a radiation imaging apparatus that radiates a radiation onto an object to detect the radiation that transmits the object, and particularly, to a radiation imaging apparatus that uses an optical element that parallelizes the radiation which travels in a divergence manner.

2. Related Background Art

In an X-ray imaging apparatus including a single X-ray source, a distance between the X-ray source and the object is set based on a size of the object and a divergence angle of the X-ray source. If the distance between the X-ray source and the object is increased in order to obtain a required resolution, the size of the apparatus is increased and brightness is lowered. In order to remove such troubles, a technology is known, where an X-ray optical element such as a capillary is used to efficiently collect X-rays to create a high intensity X-ray and capture an image in a short time. Japanese Patent Application Publication (Translation of PCT Application) No. H10-508947 discloses an optical system including an optical element obtained by bundling minute glass tubes (referred to as capillaries). The X-ray is parallelized by the capillary so that the lowering of brightness caused by the increase in the distance where the X-ray reaches the object is restricted. Further, Japanese Patent Application Laid-Open No. 2004-89445 discloses an X-ray image capturing system in which X-ray sources are two-dimensionally disposed and combined with a capillary that restricts the divergence of a generated X-ray to form an image.

An optical element in which the capillaries are bundled is formed by an assembly of minute glass tubes manufactured by a hot drawing. Therefore, it is difficult to manufacture an assembly of capillaries having a large outer diameter (several tens centimeters) which may project a human body with a high precision.

Further, in a configuration in which a plurality of small capillaries is two-dimensionally disposed, X-ray generating sources also need to be two-dimensionally disposed. Therefore, the X-ray generating sources that use high power are two-dimensionally controlled, which causes the complexity of a control system.

The invention provides a radiation imaging apparatus that has a simple structure that efficiently parallelizes a generated radiation, restricts the lowering of the brightness without depending on the size of the object, and reduces the size of the apparatus.

SUMMARY OF THE INVENTION

According to the present invention there is a radiation imaging apparatus which includes a radiation source; a reflective structure in which at least three reflective substrates are arranged with an interval and radiations which are incident into a plurality of passages, both sides of each passage being put between the reflective substrates, are reflected and parallelized by the reflective substrate at both sides of the passage to be emitted from the passage; a radiation detector; and an image construction unit that constructs an image of the object based on an intensity of the radiation which is emitted from each of the passages, transmits the object, and is detected by the radiation detector. When one edge of the reflective structure is an inlet of the radiation and the other edge is an outlet of the radiation, a pitch of the reflective substrates at the outlet is larger than a pitch of the reflective substrates at the inlet.

According to the present invention, the reflective structure is used to efficiently parallelize the radiation and obtain the high brightness regardless of the size of the object even though the distance between an X-ray source 1 and an X-ray detector 4 is short. Therefore, it is possible to reduce a size of the apparatus, capture an image at a high speed, and reduce power consumption.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Hereinafter, the present invention will be described with an example that uses an X-ray as a radiation and a slit lens as a radiation reflective structure (hereinafter, referred to as a reflective structure).

(1) Slit Lens

Figure 1:
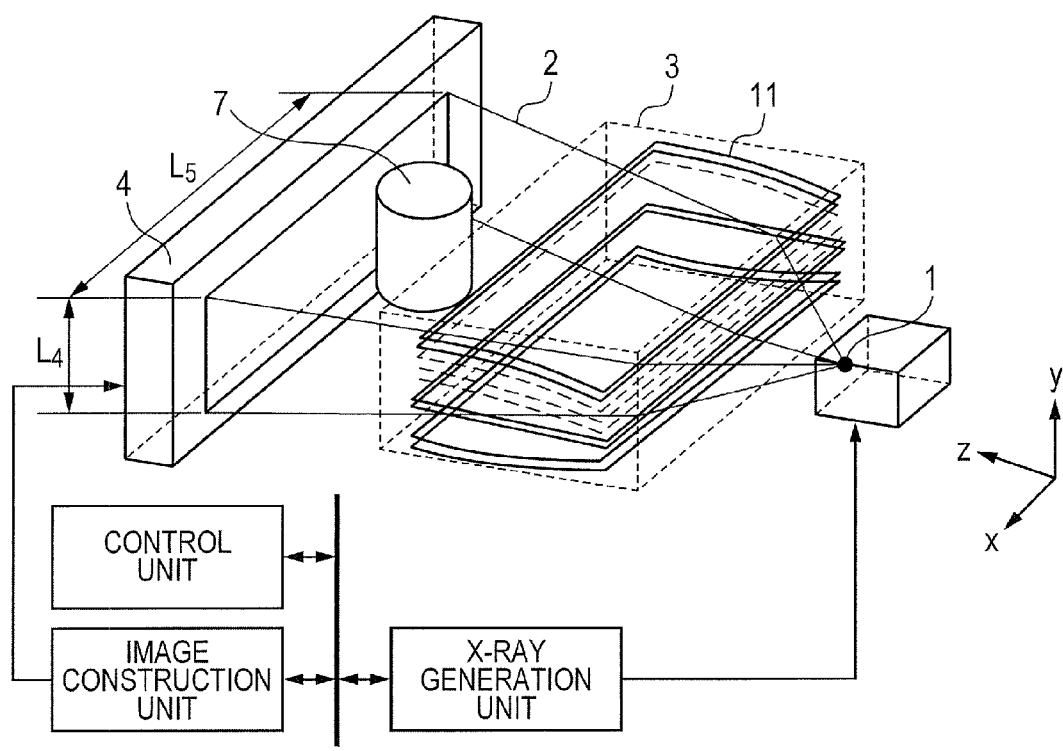
FIG. 1 is a schematic diagram illustrating a radiation imaging apparatus according to an exemplary embodiment of the present invention.
Figure 9A:
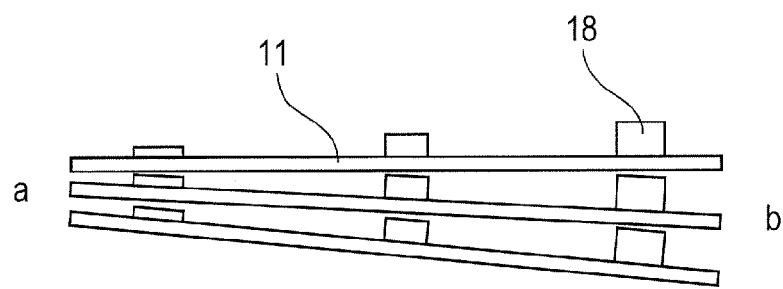
FIG. 9A is a schematic diagram illustrating a structure of a reflective structure according to an exemplary embodiment of the present invention.
Figure 9B:
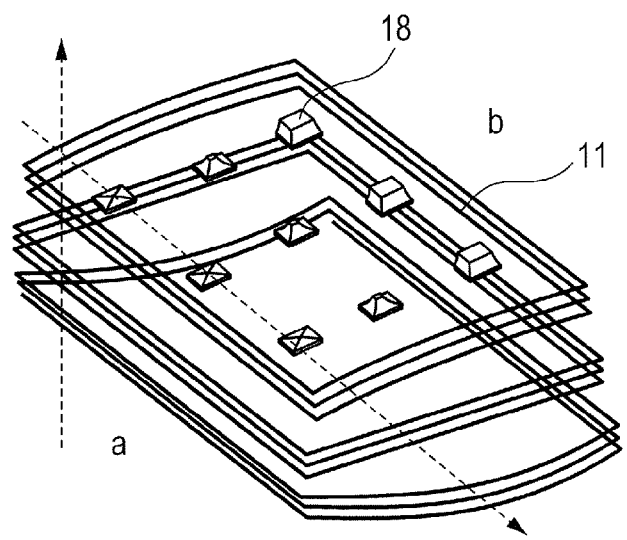
FIG. 9B is a schematic diagram illustrating a structure of a reflective structure according to an exemplary embodiment of the present invention.

As illustrated in FIG. 1, a slit lens 3 has a structure in which at least three X-ray reflective substrates (hereinafter, referred to as reflective substrate) 11 are laminated with an interval (gap) therebetween so as to match both edges thereof. For example, each of the reflective substrates 11 has a constant thickness and the at least three reflective substrates have the same thickness. As illustrated in FIGS. 9A and 9B, spacers 18 having different heights are disposed between the adjacent reflective substrates. By the spacers 18, the reflective substrates 11 are formed such that an interval at an outlet b of the X-ray which is one edge of the slit lens 3 is larger than an interval at an inlet a of the X-ray which is the other edge of the slit lens 3. The interval between the reflective substrates 11 is gradually increased from the inlet of the X-ray to the outlet of the X-ray. The spacers 18 have a pillar shape (for example, a quadrangular prism) and are disposed between the reflective substrates 11 with a predetermined interval. Further, the spacers 18 are disposed at the same position on the different layers of reflective substrates 11 (disposed at the overlapping position). The spacers 18 are disposed so as to be bonded with the reflective substrates 11. However, the reflective substrates 11 and the spacers 18 may be integrally formed by etching a glass substrate. Further, in FIG. 9A, even though the reflective substrates 11 are illustrated as a flat substrate, actually, the reflective substrates 11 may be laminated so as to be curved with a predetermined curvature as illustrated in FIG. 9B.

Radiations 2 which are incident into a plurality of passages whose both sides are put between the reflective substrate 11 are reflected from the reflective substrate 11 at both sides of each of the passages and parallelized to be emitted from the passages. When one edge of the reflective substrate 11 in the slit lens 3 is an inlet of the radiation and the other edge is an outlet of the radiation, a pitch of the reflective substrates 11 at the outlet is larger than a pitch of the reflective substrates 11 at the inlet. Here, the pitch refers to a distance between top surfaces or bottom surfaces of the adjacent reflective substrates. The "parallelization" in the present invention means that a radiation component in a laminated direction (y direction) of the reflective substrate 11 is reduced so that the emission direction of the radiation matches (collimates) with a plane (xz plane) perpendicular to the y direction.

(2) Resolution

Figure 2A:
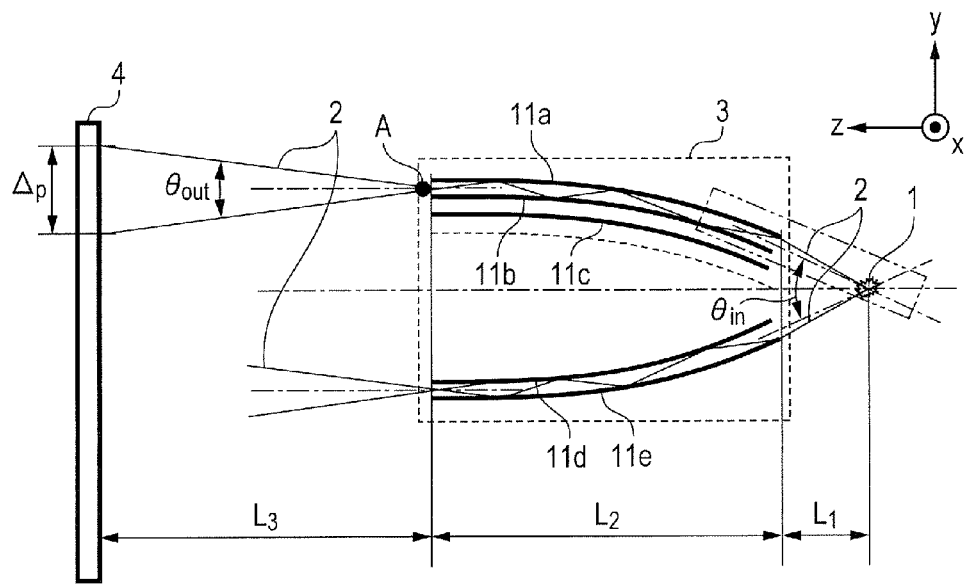
FIG. 2A is a schematic diagram illustrating a reflective structure according to an exemplary embodiment of the present invention.

First, in the X-ray imaging apparatus according to an exemplary embodiment, a penumbra amount (resolution) will be described with reference to FIGS. 1 and 2A, which is generated when an X-ray that is incident into the passage in the slit lens 3 from the X-ray source 1 and emitted from the passage is irradiated onto a sample to project a transmission image onto an X-ray detector 4. FIG. 1 is a view illustrating an overall X-ray imaging apparatus and FIG. 2A is a cross-section view of an YZ plane that passes through the X-ray source 1 of the X-ray imaging apparatus.

If there is an infinitely small object A at the outlet of the slit lens 3 and a defocused state of an image that transmits the object A is defined as a penumbra amount $\Delta_p$ of the image, the penumbra amount $\Delta_p$ is represented by Equation 1 using a divergence angle $\theta_{out}$ of the X-ray at the outlet of the slit lens 3 and a distance $L_3$ between the outlet of the slit lens 3 and the X-ray detector 4 in an opposite direction.

$$\Delta_p = L_3 \times \theta out \quad \text{(Equation 1)}$$

Equation 1 is established with respect to the X-ray which is emitted from each of the passages.

The resolving power of an X-ray imaging apparatus is lowered as the penumbra amount $\Delta_p$ is increased. Therefore, in order to increase the resolving power, if the distance $L_3$ is constant, it is important to lower the divergence angle $\theta_{out}$. In other words, it is important to increase the degree of parallelization of the X-rays which are emitted from the passages in the slit lens 3.

The resolving power of the X-ray imaging apparatus is determined by not only the penumbra amount $\Delta_p$ but also larger one of the penumbra amount $\Delta_p$ and a pixel size $\Delta_d$ of the X-ray detector 4 (for example, flat panel detector (FPD)). If the pixel size $\Delta_d$ is small, the X-ray detector 4 becomes expensive and it takes time to perform data transfer processing. In the meantime, if the penumbra amount $\Delta_p$ is lowered, for example, a size of the X-ray source 1 is required to be reduced, so that a load applied to an optical system is increased as described below. Therefore, it is important to keep a balance between the pixel size $\Delta_d$ and the penumbra amount $\Delta_p$. If an acceptable range of a ratio of the pixel size $\Delta_d$ and the penumbra amount $\Delta_p$ is 2, the following Equation 2 is established.

$$0.5 < \Delta_p/\Delta_d < 2 \quad \text{(Equation 2)}$$

(3) Parallelization Principle

Figure 2B:
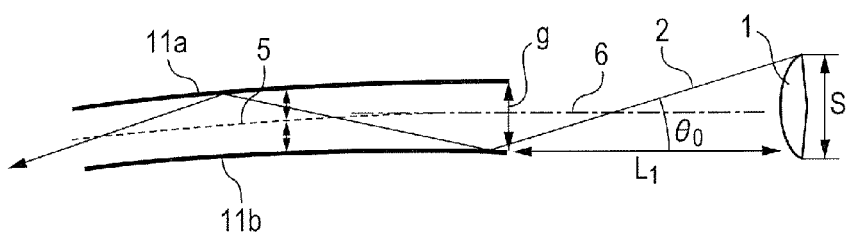
FIG. 2B is an enlarged view of a region enclosed by a two-dot chain line of FIG. 2A of the present invention.

A principle (parallelization principle) of parallelizing the X-rays, which are emitted from the passages in the slit lens 3, will be described with reference to FIG. 2B. FIG. 2B is an enlarged view of a region in the X-ray imaging apparatus illustrated in FIG. 2A enclosed by a two-dot chain line. Even though a thin glass plate is used as the reflective substrate 11, the reflective substrate 11 may be metal.

The X-ray 2 which is emitted from the X-ray source 1 is divergence light and is radiated in all directions. An X-ray source illustrated in FIG. 3 may be used as the X-ray source 1. The slit lens 3 is disposed so as to be separated by a distance $L_1$ from the X-ray source 1. The slit lens 3 is arranged such that the thin glass plates having a gentle curvature are arranged with predetermined intervals and a pitch of the thin glass plates at the outlet of the X-ray is larger than a pitch at the inlet of the X-ray. 10 to 1,000 sheets of thin glass plates each having a thickness of 1 µm to 100 µm are laminated and the X-ray is reflected from both sides of the thin glass plate. An X-ray 2, which is incident into the passage between the thin glass plates 11a and 11b, travels while being reflected from both the thin glass plates 11a and 11b and then is emitted from the passage. Similarly in the passage between the thin glass plates 11b and 11c, the incident X-ray travels while being reflected from both the thin glass plates 11b and 11c and then is emitted from the passage, which is similar in a passage between other adjacent thin glass plates. Most of the X-rays 2 which are incident into the passages are parallelized as described above. However, among the X-rays 2 which are incident into the passages, an X-ray which travels in a parallel direction is not reflected from the thin glass plate but is directly emitted from each of the passage.

As described above, as the X-ray travels in the passage in the slit lens 3, an X-ray whose traveling direction is not a parallel direction is reflected multiple times from the thin glass plate so that the traveling direction is gradually close to the parallel direction. Then, the X-ray is parallelized and emitted from the passage. Further, an X-ray which travels in the parallel direction is directly emitted from each of the passages. Accordingly, it is possible to efficiently parallelize the X-ray to be emitted with a simple structure. By doing this, the penumbra amount $\Delta_p$, which is formed on the X-ray detector 4, becomes smaller.

Here, a virtual plane 5 is set in a position which is separated from the thin glass plates at both sides of the passage with the same distance and a tangential plane 6 of the virtual plane 5 at the inlet of the slit lens 3 is considered. If the X-ray source 1 is disposed on tangential planes of a plurality of virtual planes 5 at the inlet side, more X-rays may be incident into the passages. In case of the X-ray source 1 illustrated in FIG. 3, a part that generates an X-ray with a light source size s may be disposed on the tangential planes of the plurality of virtual planes 5 at the inlet side. As illustrated in FIG. 2A, if all tangential planes of the plurality of virtual planes 5, which are set between adjacent thin glass plates, at the inlet side intersect on the common straight line and the X-ray source 1 is disposed on the straight line, the size of the X-ray source 1 may be reduced. Further, if the thin glass plates at the outlet of the slit lens 3 are parallel, that is, if the tangential planes 6 of the plurality of virtual planes 5 at the outlet side are approximately parallel, the degree of parallelization of the X-rays emitted from the passages may be increased.

Figure 4:
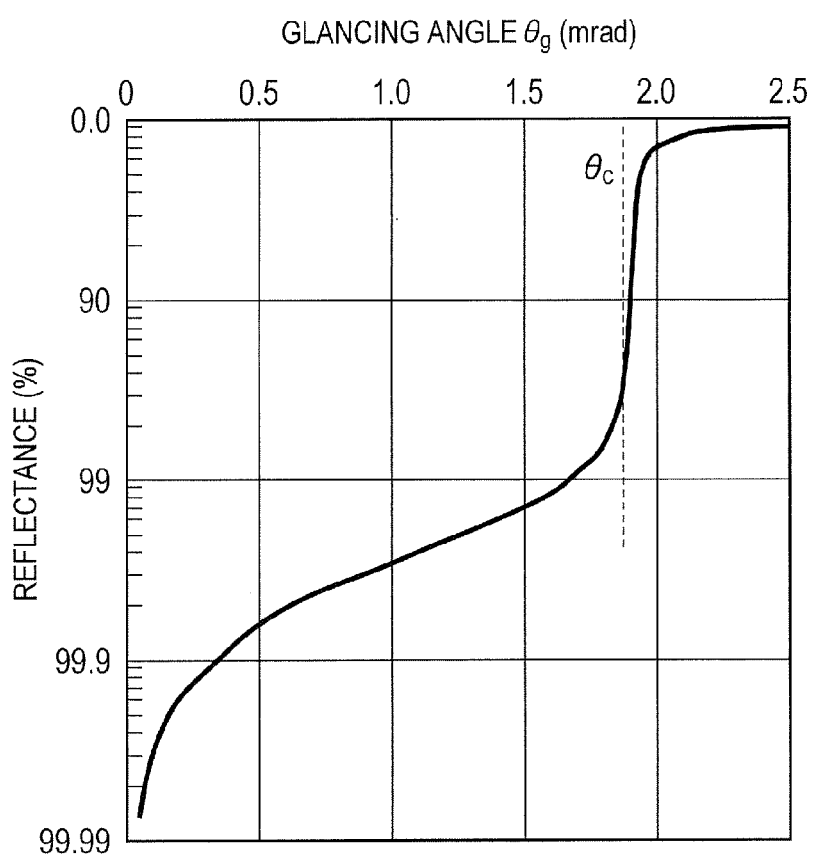
FIG. 4 is a graph illustrating a reflectance of the radiation of a quartz substrate.

FIG. 4 illustrates an X-ray reflectance of a quartz substrate with respect to an X-ray having a wavelength of 0.071 nm. A horizontal axis is a glancing angle $\theta_g$ at which the X-ray is incident onto each of the passages and a vertical axis is a reflectance of the X-ray. When the glancing angle $\theta_g$ is 0.5 mrad, the reflectance of the X-ray is 99.8% or higher. Therefore, it is understood that 90% or more of the X-rays pass the slit lens 3 even if the X-rays are reflected 50 times. Further, referring to FIG. 4, when the glancing angle $\theta_g$ is 1.8 mrad, the reflectance of the X-ray is rapidly attenuated. In this case, the glancing angle $\theta_g$ is referred to as a critical angle and denoted by $\theta_c$. When the X-ray source 1 is disposed on the tangential planes 6 of the plurality of virtual planes 5 at the inlet side, if the angular deviation of the tangential planes 6 is increased, a deviation in an angle at which each of the thin glass plates brings to the X-ray source 1 into view is generated. Then, the X-ray 2 which is emitted from the X-ray source 1 is not reflected on a position where the glancing angle $\theta_g$ is larger than the critical angle $\theta_c$ in the thin glass plate. Accordingly, when a distance between the X-ray source 1 and the inlet of the slit lens 3 in the opposite direction is $L_1$ and a critical angle of the glancing angle $\theta_g$ at which the X-ray is incident onto the passage is $\theta_c$, the distance $\Delta_s$ between the X-ray source 1 and the passage in a direction perpendicular to the opposite direction needs to satisfy the following Equation 3.

$$\Delta_s < L_1 \times \theta_c \quad \text{(Equation 3)}$$

Therefore, it is required to determine a relative position of the slit lens 3 and the X-ray source 1, that is, a relative position of the thin glass plate and the X-ray source 1 so as to satisfy Equation 3. In case of the X-ray source 1 illustrated in FIG. 3, $L_1$ indicates a distance between the part that generates the X-ray having a light source size s and the inlet of the slit lens 3 in an opposite direction and $\Delta_s$ indicates a distance between the part that generates the X-ray and the passage in a direction perpendicular to the opposite direction.

Here, the slit lens 3 will be described, in which the interval between adjacent thin glass plates is constant and all thin glass plates are formed such that a thickness at the outlet side is larger than a thickness at the inlet side as illustrated in FIG. 2A. Such a slit lens 3 may be manufactured by laminating thin glass plates having a wedge shaped thickness. In this case, a maximum glancing angle $\theta_{gmax}$ at which the X-ray is incident onto the passage and is reflected from the thin glass plate is represented by Equation 4.

$$\theta_{gmax} = (s+g)/2L_1 \quad \text{(Equation 4)}$$

Here, s indicates a size of the X-ray source 1 (diameter of the light source) and is $2\sigma$ when an intensity distribution of the light source may be approximated by a Gaussian distribution. g is an interval (gap) between adjacent thin glass plates. However, $\theta_{gmax}$ needs to be smaller than the critical angle $\theta_c$.

If the thin glass plates are parallel to each other at the outlet of the slit lens 3, the divergence angle $\theta_{out}$ of the X-ray which is emitted from each of the passages in the slit lens 3 is represented by Equation 5.

$$\theta_{out} = 2 \times \theta_{gmax} \quad \text{(Equation 5)}$$

In this case, the penumbra amount $\Delta_p$ is represented by Equation 6 based on Equations 1, 4, and 5.

$$\Delta_p = L_3 \times (s+g)/L_1 \quad \text{(Equation 6)}$$

Further, Equation 7 is established based on Equations 2 and 6.

$$0.5 \times \Delta_d < L_3 \times (s+g)/L_1 < 2 \times \Delta_d \quad \text{(Equation 7)}$$

If the degree of parallelization of the thin glass plate is lowered, the X-ray does not reach a pixel of the X-ray detector 4 that detects an intensity of the X-ray or a pixel having an extremely weak X-ray intensity is generated. In order to remove such troubles, the parallelism $\Delta_{out}$ of all the thin glass plates needs to satisfy larger one of an acceptable value $\Delta_{out-a}$ in the following Equation 8a and an acceptable value $\Delta_{out-b}$ in the following Equation 8b. Here, $\Delta_d$ indicates a pixel size of the X-ray detector 4.

$$\Delta_{out-a} < (s+g)/L_1 \quad \text{(Equation 8a)}$$

$$\Delta_{out-b} < \Delta_d/L_3 \quad \text{(Equation 8b)}$$

Figure 5:
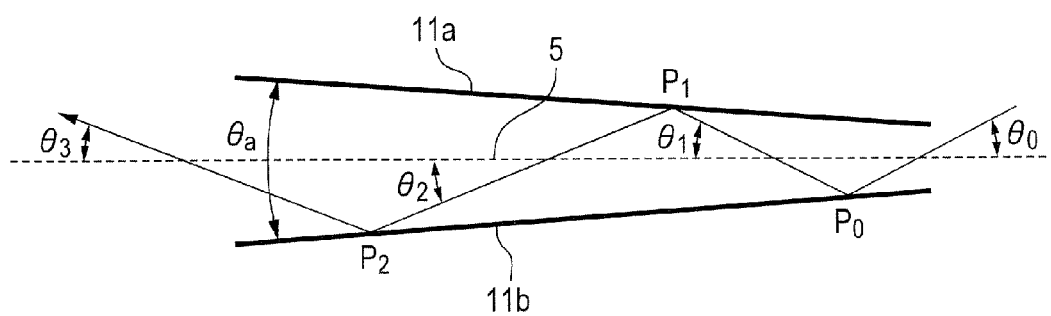
FIG. 5 is a schematic diagram illustrating a reflective structure according to another exemplary embodiment of the present invention.

Next, a slit lens 3 will be described, in which thicknesses of all thin glass plates are constant and an interval between adjacent thin glass plates at the outlet side is larger than an interval at the inlet side. In order to simplify the description, a straight guide is considered, in which the thin glass plates 11a and 11b form an angle $\theta_a$ as illustrated in FIG. 5. If an angle formed by the virtual plane 5 and the X-ray 2 is referred to as a half divergence angle, an X-ray which is incident into the passage between the thin glass plates 11a and 11b with the half divergence angle $\theta_0$ ($0.5 \times \theta_a < \theta_0 < \theta_c$) is reflected at a point $P_0$ of the thin glass plate 11b and then reflected at a point $P_1$ of the thin glass plate 11a. A half divergence angle $\theta_1$ after the first reflection is represented by Equation 9.

$$\theta_1 = \theta_0 - \theta_a \quad \text{(Equation 9)}$$

Therefore, the angle $\theta_n$ after n-th reflection is represented by Equation 10 in a range of "$\theta_0 - n \times \theta_a > 0$".

$$\theta_n = \theta_0 - n \times \theta_a \quad \text{(Equation 10)}$$

If $\theta_n < 0.5 \times \theta_a$, the X-ray 2 does not reach the thin glass plate, so that the half divergence angle is not be varied. Further, if an interval between the adjacent thin glass plates at the outlet side is $g_{out}$, an interval between the adjacent thin glass plates at the inlet side is $g_{in}$, and a length of the thin glass plate is $L_2$, Equation 11 is established.

$$\theta_a = (g_{out} - g_{in})/L_2 \quad \text{(Equation 11)}$$

In this case, since $\theta_a < \theta_{out}$, the penumbra amount $\Delta_p$ is represented by Equation 12 based on Equations 1 and 11.

$$(g_{out} - g_{in}) \times L_3/L_2 < \Delta_p \quad \text{(Equation 12)}$$

Further, Equation 13 is established based on Equations 2 and 12.

$$0.5 \times \Delta_d < L_3 \times (g_{out} - g_{in})/L_2 < 2 \times \Delta_d \quad \text{(Equation 13)}$$

for the same reason as the above mentioned reason with respect to the slit lens 3 having the structure illustrated in FIG. 2A, even in a slit lens 3 in which thicknesses of all thin glass plates are constant and an interval between adjacent thin glass plates at the outlet side is larger than an interval at the inlet side, the thin glass plates at the outlet of the slit lens 3 may be parallel to each other. Therefore, the parallelism $\Delta_{out}$ of all the thin glass plates needs to satisfy larger one of an acceptable value $\Delta_{out-a}$ in the following Equation 14a and an acceptable value $\Delta_{out-b}$ in the following Equation 14b. Here, $\Delta_d$ indicates a pixel size of the X-ray detector 4.

$$\Delta_{out-a} < (g_{out} - g_{in})/L_2 \quad \text{(Equation 14a)}$$

$$\Delta_{out-b} < \Delta_d/L_3 \quad \text{(Equation 14b)}$$

In the meantime, a penumbra amount $\Delta_x$ in a dimension where the thin glass plate does not have a curvature, that is, a direction (x-direction) perpendicular to both an opposite direction between the X-ray source 1 and the inlet of the slit lens 3 and a direction perpendicular to the opposite direction between the X-ray source 1 and the passage is represented by Equation 15 and determined by the relative position of the slit lens 3, the X-ray source 1, and the X-ray detector 4.

$$\Delta_x = s \times L_3 / (L_2 + L_1) \quad \text{(Equation 15)}$$

Further, a slit lens 3, where the X-ray source 1 is disposed on the tangential planes of the plurality of virtual planes 5 at the inlet side and the tangential planes of the plurality of virtual planes at the outlet sides intersect at a common straight line, may also be applied to the present invention. The parallelization of the X-ray may be embodied with this structure. Further, if all tangential planes 6 of the plurality of virtual planes 5 at the inlet side intersect at a common straight line and the X-ray source 1 is disposed on the straight line, a size of the X-ray source 1 can be reduced. In this case, the common straight line intersecting at the inlet side is a different line from the common straight line intersecting at the outlet side.

(4) X-Ray Source

Figure 3:
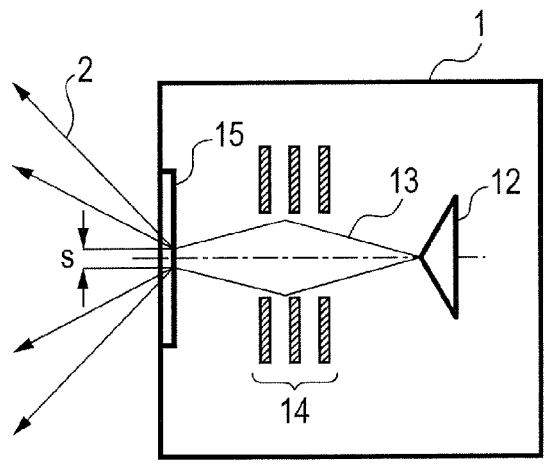
FIG. 3 is a schematic diagram illustrating a radiation source according to an exemplary embodiment of the present invention.

As the X-ray source 1, a reflective X-ray source that radiates an electron generated from a cathode obliquely to an anode target and takes the X-ray at approximately 90 degrees from an electron incident direction is generally used. However, in the present invention, since a minute beam diameter is required in order to focus light of the slit lens 3 and reduce a defocused state, a transmissive X-ray source as illustrated in FIG. 3 can be used. In the transmissive X-ray source 1 illustrated in FIG. 3, an electron beam 13 radiated from an electron beam source 12 is converged by an electron lens 14 for converging an electron to be focused on a target 15. A size of the electron beam 13 may be easily varied by changing a power of the electron lens 14. Therefore, it is possible to adjust the size s of the X-ray source 1.

In order to capture a still image, at least an X-ray generating voltage, an X-ray generation time and an amount of electronic current are controlled. However, in CT imaging, a timing of the X-ray generation is especially important. Therefore, in the CT imaging, the X-ray imaging apparatus may have a structure in which not only the X-ray generating voltage, the X-ray generation time and the amount of electronic current, but also the timing of the X-ray generation are controlled.

(5) X-Ray Detector

In an exemplary embodiment, a generally known X-ray detector is used. In the still image capturing, one of an X-ray film, an X-ray image intensifier which is called as II and a method that visualizes and digitalizes a latent image of the X-ray with a laser, which is referred to as a CR, is used. In CT imaging, a flat panel detector which is abbreviated as FPD or an area photo sensor which is arranged to be sensitive to the X-ray may be used.

(6) Image Construction Unit

The image construction unit constructs an image of the object based on an intensity of the X-ray which is emitted from each of the passages, transmits the object, and is detected by the X-ray detector. The image construction unit inputs a signal from the X-ray detector in accordance with the timing of the X-ray generation to construct as an image, performs image processing such as denoising and then controls output to a monitor.

(7) Brightness of System

Approximate system brightness according to a structure of the exemplary embodiment of the present invention will be described. Here, the system brightness refers to a brightness of the radiation which is emitted from the radiation source and detected by the radiation detector in the radiation imaging apparatus. When the slit lens 3 is not used, if the output from the X-ray source 1 is constant, the brightness of the X-ray is generally correlated with a projected area ($L_4 \times L_5$ on FIG. 1) in a distance from the X-ray source 1 to the X-ray detector 4 ($L_1 + L_2 + L_3$ on FIG. 2A). $L_4$ is a length of the projected area in the y direction and $L_5$ is a length of the projected area in the x direction. In the meantime, in the projected area when the slit lens 3 is used as in the exemplary embodiment, since the X-ray after being emitted from the slit lens 3 is parallelized to a plane being perpendicular to the y direction, an intensity when the X-ray is incident into the slit lens 3 is substantially maintained. Therefore, the projected area is "$L_1 \times \theta_{in} \times L_5$". As the projected area is small, a brighter image may be obtained. Therefore, in the structure includes the slit lens 3 in according to the exemplary embodiment, since "$L_1 \times \theta_{in} < L_4$" may be satisfied, a bright image system can be arranged. If the order of the thickness t of the thin glass plate is same as the order of the interval (gap) g between adjacent thin glass plates in according to the exemplary embodiment, an approximate system brightness may be obtained by multiplying an amount of the X-ray and an attenuation rate based on an aperture ratio T ($=g/(t+g)$).

As described above, in the present invention, the projected area may be reduced by using the slit lens 3. Therefore, even though the distance between the X-ray source 1 and the X-ray detector 4 is small, the high brightness may be obtained regardless of the size of the object. Therefore, the size of the apparatus may be reduced.

First Exemplary Embodiment

An X-ray imaging apparatus according to the exemplary embodiment captures a still image. An X-ray generating voltage, an amount of electronic current and a timing of an X-ray generation are controlled by an X-ray generation unit illustrated in FIG. 1. An image construction unit in the exemplary embodiment inputs a signal from the X-ray detector in accordance with the timing of the X-ray generation to construct an image, performs image processing such as denoising and then controls output to a monitor. Therefore, the timing of the X-ray generation is required to be synchronized with a timing of constructing an image and the synchronization processing is performed by a control unit.

As illustrated in FIG. 2A, the exemplary embodiment includes a slit lens 3 where an interval g between the adjacent thin glass plates is constantly 10 μm, and a thickness of all thin glass plates is 20 μm at the outlet side and 10 μm at the inlet side.

An X-ray 2 radiated from the X-ray source 1 is incident into a passage between thin glass plates 11a and 11b and travels while being reflected from both the thin glass plates 11a and 11b, which is similar in a passage between other adjacent thin glass plates. A solid angle Ω1 of the X-ray which is incident into one passage is proportional to the interval g. However, since the plurality of thin glass plates is arranged so as to be spaced apart from each other with the interval g, even though the interval g is small, the entire amount of X-ray introduced into the passage is proportional to a divergence angle $\theta_{in}$ and an aperture ratio. Here, the "aperture ratio" refers to a ratio of the gap which occupies in the inlet of the slit lens 3 and the aperture ratio in the exemplary embodiment is 50% ($=10$ μm/(10 μm+10 μm)). For this reason, 50% of X-ray 2 which is radiated from the X-ray source 1 with the divergence angle $\theta_{in}$ or smaller is incident into the passage, travels while being reflected from the thin glass plates and is radiated from the passage with the divergence angle $\theta_{out}$. An image of the object which is disposed between the outlet of the slit lens 3 and the FPD is projected onto the FPD by the radiated X-ray. In this case, a penumbra amount $\Delta_p$ of the image of the object is formed on the FPD, so that the resolution is lowered in accordance with Equation 1.

A method that restricts the lowering of resolution in a predetermined range will be described. Since the penumbra amount $\Delta_p$ is represented by Equation 6, a size s of the X-ray source 1 is represented by Equation 16 based on Equations 2 and 6.

$$0.5 \times L_1/L_3 \times \Delta_d - g < s < 2 \times L_1/L_3 \times \Delta_d - g \qquad \text{(Equation 16)}$$

When a distance $L_1$ between the X-ray source 1 and the inlet of the slit lens 3 in the opposite direction is 100 mm, a distance $L_3$ between the outlet of the slit lens 3 and the FPD in the opposite direction is 200 mm and a pixel size $\Delta_d$ of the FPD is 100 μm, an acceptable range of the size s of the light source is "15 μm<s<90 μm". The size s of the light source is required to be adjusted within the acceptable range.

In the meantime, when the length $L_2$ of the slit lens 3 is 100 mm and the size s of the light source is 90 μm, the penumbra amount $\Delta_x$ is 90 μm in accordance with Equation 15, which is almost equal to the pixel size $\Delta_d$ of the FPD.

As described above, the resolution in a direction perpendicular to both the opposite direction between the X-ray source 1 and the inlet of the slit lens 3 and a direction perpendicular to the opposite direction between the X-ray source 1 and the passage is similar to the resolution in the opposite direction between the X-ray source 1 and the inlet of the slit lens 3. Therefore, it is possible to efficiently parallelize the X-ray to be emitted and restrict the lowering of the resolution within a predetermined range using the X-ray imaging apparatus with a simple structure.

$L_4$ and $L_5$ are arbitrarily determined depending on the size of the object to be captured. In the exemplary embodiment, $L_4$ is 10 mm and $L_5$ is 50 mm.

In the X-ray imaging apparatus according to the exemplary embodiment, first, the control unit initializes the X-ray generation unit and the image construction unit, and then the X-ray is generated for a predetermined time in accordance with the control from the X-ray generation unit. Further, FPD accumulates X-ray image information until the X-ray is completely generated. The signal is input from the FPD at the timing of the end of the X-ray generation and constructed as an image to obtain a capturing image. After obtaining the image, denoising process is arbitrarily performed.

Second Exemplary Embodiment

Figure 6:
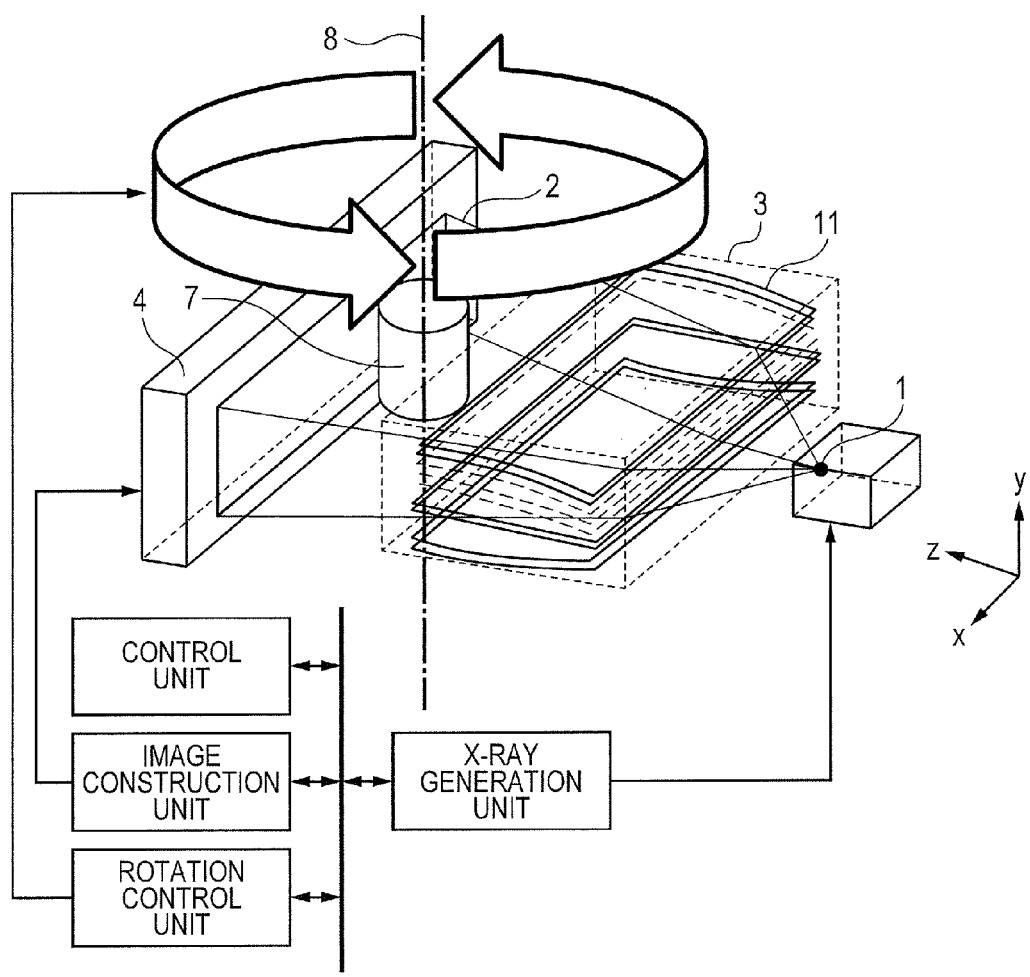
FIG. 6 is a schematic diagram illustrating a radiation imaging apparatus according to another exemplary embodiment of the present invention.

An X-ray imaging apparatus according to the exemplary embodiment is an X-ray CT imaging apparatus including a mechanism that rotates the X-ray source 1, the slit lens 3, and the FPD which are the components of the first exemplary embodiment as one unit around an axis 8 as a rotational center axis as illustrated in FIG. 6. A rotation control unit that precisely controls a rotational angle is added as a mechanism. The intensity of the X-ray that transmits the object is detected by the FPD in accordance with the rotational angle controlled by the rotation control unit. The image construction unit constructs a three-dimensional image of the object based on the intensity of the X-ray obtained in accordance with the rotational angle. Here, a normal direction of an emission direction of the X-ray which is parallelized by the slit lens 3 is the rotational axis.

In the X-ray imaging apparatus according to the exemplary embodiment, first, the control unit initializes the X-ray generation unit, the image construction unit and the rotation control unit, and then the X-ray is generated for a predetermined time in accordance with the control from the X-ray generation unit. Further, the FPD accumulates X-ray image information until the X-ray is completely generated. A signal is input from the FPD at a timing of the end of the X-ray generation. As a next step, the above-mentioned unit is rotated by a predetermined angle. A onetime rotational angle is determined as an arbitrary angle required to construct a necessary image. Generally, the onetime rotational angle is approximately 1 to 10 degrees. After moving by a predetermined angle, the X-ray is repeatedly generated and input necessary times. After capturing all images, the image is three-dimensionally reconstructed to obtain a CT imaging image.

Even though, in the exemplary embodiment, a body axis of the object and the rotational axis of the above-mentioned unit are matched to each other, both axes do not need to be matched in the CT imaging and the invention is not limited to this configuration.

Third Exemplary Embodiment

Figure 7:
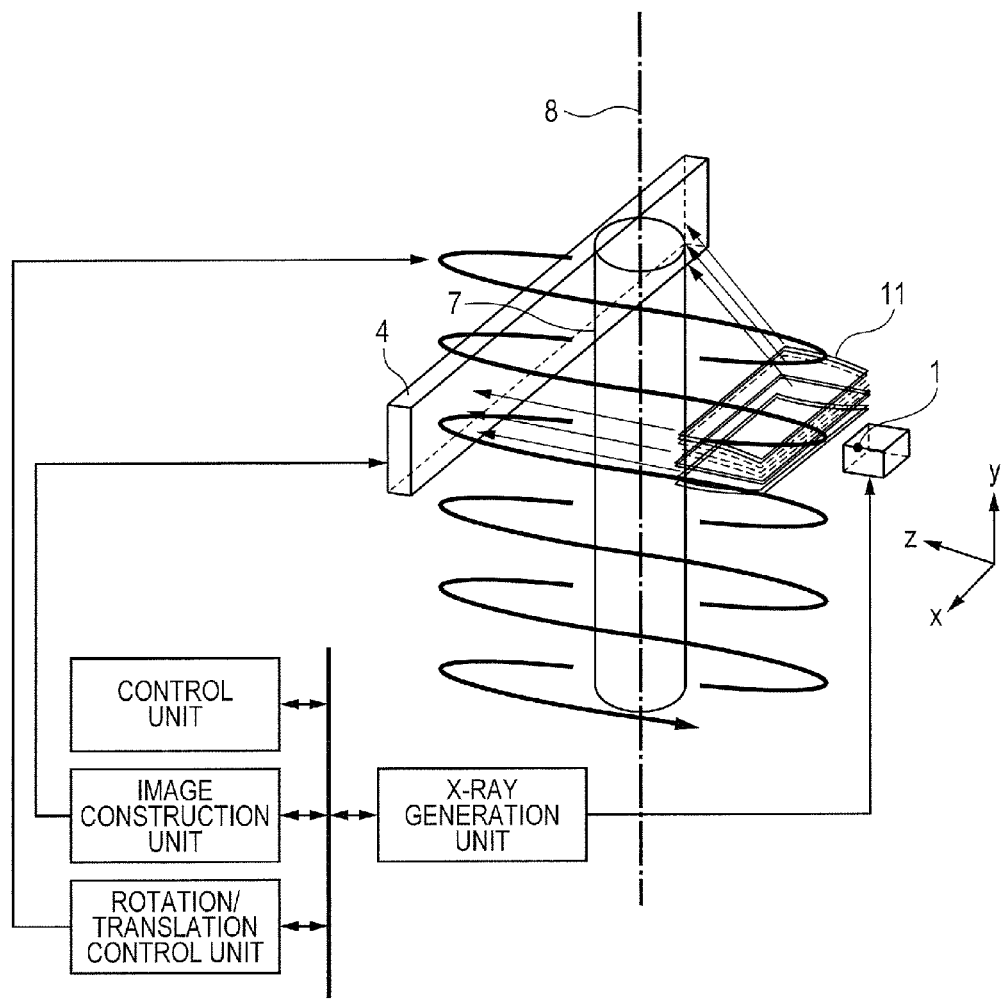
FIG. 7 is a schematic diagram illustrating a radiation imaging apparatus according to another exemplary embodiment of the present invention.

An X-ray imaging apparatus according to the exemplary embodiment is an X-ray CT imaging apparatus further including a translation mechanism in addition to the structure of the second exemplary embodiment as illustrated in FIG. 7. The X-ray CT imaging apparatus includes the mechanism that rotates the X-ray source 1, the slit lens 3, and the FPD as one unit around the axis 8 as a rotational central axis and a translational moving mechanism that moves the above-mentioned unit in the same direction as a body axis 8 of the object. Therefore, the X-ray CT imaging apparatus includes a rotation and translation control unit that controls the rotation and the translational movement. The translational movement is performed so as to be synchronized with the angular movement of the rotation, so that the unit spirally moves. The intensity of the X-ray that transmits the object is detected by the FPD in accordance with the rotational angle and the movement distance controlled by the rotation and translation control unit. The image construction unit constructs a three-dimensional image of the object based on the intensity of the X-ray obtained in accordance with the rotational angle and the movement distance.

In the X-ray imaging apparatus according to the exemplary embodiment, first, the control unit initializes the X-ray generation unit, the image construction unit and the rotation and translation control unit, and then the X-ray is generated for a predetermined time in accordance with the control from the X-ray generation unit. Further, the FPD accumulates X-ray image information until the X-ray is completely generated. A signal is input from the FPD at a timing of the end of the X-ray generation. As a next step, the above-mentioned unit is rotated by a predetermined angle and simultaneously moves by a predetermined distance in an axial direction. A onetime rotational angle is determined as an arbitrary angle required to construct a necessary image. Generally, the onetime rotational angle is approximately 1 to 10 degrees. Further, the onetime translational movement distance depends on a thickness of the slit lens 3 at the outlet side. However the onetime translational movement distance may be determined by an arbitrary movement amount required to construct a necessary image. After translationally moving by a predetermined angle and a predetermined amount, the X-ray is repeatedly generated and detected necessary times. After capturing all images, the image is three-dimensionally reconstructed to obtain a CT imaging image.

Fourth Exemplary Embodiment

Figure 8:
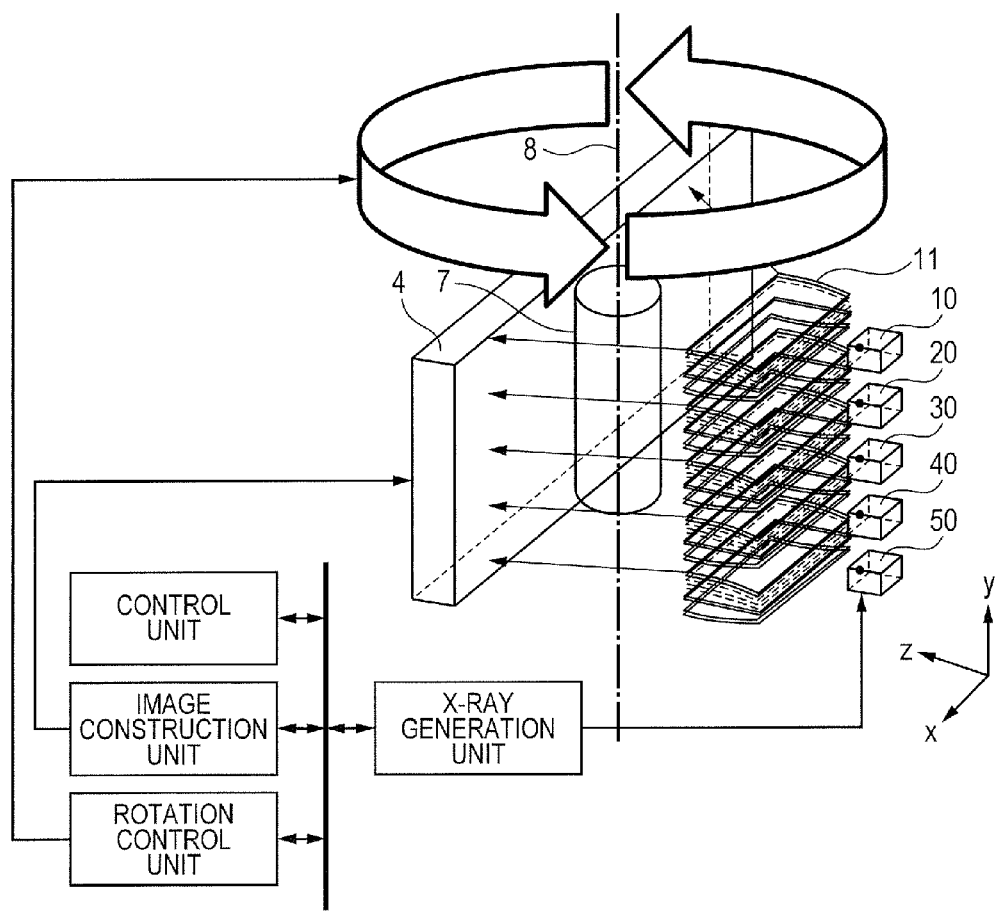
FIG. 8 is a schematic diagram illustrating a radiation imaging apparatus according to another exemplary embodiment of the present invention.

An X-ray imaging apparatus of the exemplary embodiment is an X-ray CT imaging apparatus in which the X-ray source 1 and the slit lens 3 are integrated as one radiation unit in the structure of the second exemplary embodiment and a plurality of radiation units is disposed with an interval in an rotational axis direction as illustrated in FIG. 8. The X-ray CT imaging apparatus includes a mechanism that rotates the plurality of radiation units and one FPD as an integrated detecting system around an axis 8 as a rotational center axis.

In the X-ray imaging apparatus according to the exemplary embodiment, first, the control unit initializes a plurality of X-ray generation units, an image construction unit and a rotation control unit, and then X-rays are generated for a predetermined time by the plurality of X-ray sources 1 at the same instant in accordance with the control from the X-ray generation unit. Further, the FPD accumulates X-ray image information until the X-ray is completely generated. A signal is input from the FPD at a timing of the end of the X-ray generation. As a next step, the above-mentioned radiation unit is rotated by a predetermined angle. A onetime rotational angle is determined as an arbitrary angle required to construct a necessary image. Generally, the onetime rotational angle is approximately 1 to 10 degrees. After moving by a predetermined angle, the X-ray is repeatedly generated and detected necessary times. After capturing all images, the image is three-dimensionally reconstructed to obtain a CT imaging image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-055717, filed on Mar. 13, 2012, which is hereby incorporated by reference herein in its entirety.

What is claimed is:

1. A radiation imaging apparatus, comprising:
    a radiation source;
    a reflective structure in which
        at least three reflective substrates are arranged with an interval, and
        radiation which is incident into a plurality of passages, both sides of each passage being put between the reflective substrate, is reflected and parallelized by the reflective substrate at both sides of the passage to be emitted from the passage;
    a radiation detector; and
    an image construction unit arranged to construct an image of an object based on an intensity of the radiation which is emitted from each of the passages, transmitted through the object, and is detected by the radiation detector,
    wherein when one edge of the reflective structure is an inlet of the radiation and the other edge is an outlet of the radiation, a pitch of the reflective substrates at the outlet is larger than a pitch of the reflective substrates at the inlet,
    wherein when a virtual plane is set in a position which is separated from the reflective substrates at both sides of the passage with the same distance, the radiation source is disposed on tangential planes of a plurality of virtual planes at the inlet and the tangential planes of the plurality of virtual planes at the outlet are approximately parallel to each other, and
    wherein if the interval between adjacent reflective substrates is constant and a thickness of the reflective substrate at an outlet side is larger than a thickness of the reflective substrate at an inlet side, a penumbra amount $\Delta_p$ of the object which is formed on the radiation detector satisfies the following relation:

$$\Delta_p = L_3 \times (s+g)/L_1,$$

where $L_3$ is a distance between the outlet and the radiation detector in the opposite direction, s is a size of the radiation source, g is an interval between adjacent reflective substrates, and $L_1$ is a distance between the radiation source and the inlet in the opposite direction.

2. The radiation imaging apparatus according to claim 1, wherein if a size of the pixel of the radiation detector is $\Delta_d$, the following relation is satisfied:

$$0.5 \times \Delta_d < L_3 \times (s+g)/L_1 < 2 \times \Delta_d.$$

3. A radiation imaging apparatus, comprising:
    a radiation source;
    a reflective structure in which
        at least three reflective substrates are arranged with an interval, and
        radiation which is incident into a plurality of passages, both sides of each passage being put between the reflective substrate, is reflected and parallelized by the reflective substrate at both sides of the passage to be emitted from the passage;
    a radiation detector; and
    an image construction unit arranged to construct an image of an object based on an intensity of the radiation which is emitted from each of the passages, transmits the object, and is detected by the radiation detector,
    wherein when one edge of the reflective structure is an inlet of the radiation and the other edge is an outlet of the radiation, a pitch of the reflective substrates at the outlet is larger than a pitch of the reflective substrates at the inlet,
    wherein when a virtual plane is set in a position which is separated from the reflective substrates at both sides of the passage with the same distance, the radiation source is disposed on tangential planes of a plurality of virtual planes at the inlet and the tangential planes of the plurality of virtual planes at the outlet are approximately parallel to each other, and
    wherein if a thickness of the reflective substrate is constant, the thicknesses of the reflective substrates are equal to each other, and an interval between adjacent reflective substrates at the outlet side is larger than an interval at the inlet side, a penumbra amount $\Delta_p$ of the object which is formed on the radiation detector satisfies the following relation:

$$(g_{out} - g_{in}) \times L_3/L_2 < \Delta_p,$$

where $L_3$ is a distance between the outlet and the radiation detector in the opposite direction, $g_{out}$ is the interval between adjacent reflective substrates at the outlet side, $g_{in}$ is the interval between adjacent reflective substrates at the inlet side, and $L_2$ is a length of the reflective substrate.

4. The radiation imaging apparatus according to claim 3, wherein if a distance between the radiation source and the inlet in an opposite direction is $L_1$ and a critical angle of a glancing angle at which the radiation is incident onto each of the passages is $\theta_c$, the distance $\Delta_s$ between the radiation source and the passage in a direction perpendicular to the opposite direction satisfies the following equation:

$$\Delta_s < L_1 \times \theta_c.$$

5. The radiation imaging apparatus according to claim 3, further comprising:
- a rotation control unit that rotates the radiation source, the reflective structure and the radiation detector in a body around the object with a normal direction with respect to an emission direction of the parallelized radiation as a rotational axis,
- wherein an intensity of the radiation which transmits the object is detected by the radiation detector in accordance with the rotational angle controlled by the rotation control unit.

6. The radiation imaging apparatus according to claim 5, wherein a plurality of radiation units each of which is arranged by the radiation source and the reflective structure is disposed in the normal direction with an interval.

7. The radiation imaging apparatus according to claim 5, wherein the image construction unit constructs a three-dimensional image of the object based on the intensity of the radiation detected in accordance with the rotational angle.

8. The radiation imaging apparatus according to claim 3, further comprising:
- a rotation and translation control unit that moves the radiation source, the reflective structure, and the radiation detector in a body in a normal direction while rotating the radiation source, the reflective structure, and the radiation detector around the object with a normal direction with respect to an emission direction of the parallelized radiation as a rotational axis,
- wherein an intensity of the radiation which transmits the object is detected by the radiation detector in accordance with the rotational angle and the movement distance controlled by the rotation and translation control unit.

* * * * *